United States Patent [19]

Johnson et al.

[11] Patent Number: 5,756,468
[45] Date of Patent: *May 26, 1998

[54] PHARMACEUTICAL COMPOSITIONS OF BOTULINUM TOXIN OR BOTULINUM NEUROTOXIN AND METHODS OF PREPARATION

[75] Inventors: Eric A. Johnson, Madison; Michael C. Goodnough, Stoughton, both of Wis.

[73] Assignee: Wisconsin Alumni Research Foundation, Madison, Wis.

[ * ] Notice: The term of this patent shall not extend beyond the expiration date of Pat. No. 5,512,547.

[21] Appl. No.: 624,771

[22] Filed: Mar. 27, 1996

Related U.S. Application Data

[63] Continuation-in-part of Ser. No. 322,624, Oct. 13, 1994, Pat. No. 5,512,547.
[51] Int. Cl.⁶ .............................. A61K 38/00; C07K 1/00
[52] U.S. Cl. ................................ 514/21; 514/2; 530/350; 530/363; 530/364; 530/825
[58] Field of Search ..................... 514/21, 2; 530/350, 530/363, 364, 825

[56] References Cited

U.S. PATENT DOCUMENTS 5,512,547   4/1996   Johnson et al. ........................... 514/21

FOREIGN PATENT DOCUMENTS 0593 176A2   4/1994   European Pat. Off. .
WO94/00481   1/1994   WIPO .
WO95/05842   3/1995   WIPO .

OTHER PUBLICATIONS

Goodnough et al, *Applied & Environmental Microbiology*, vol. 58, No. 10, pp. 3426–3428, 1992.

Schantz & Johnson, "Properties and Use of Botulinum Toxin and Other Microbial Neurotoxins in Medicine", Mar. 1992, pp. 80–99.

Schantz & Johnson, "Preparation and Characterization of Botulinum Toxin Type A for Human Treatment", vol. 25, pp. 41–49, 94.

Goodnough & Johnson, "Stabilization of Clostridium Botulinum Neurotoxin During Lyophilization", Applied & Environmental Microbiology, Oct. 1992, pp. 3426–3428.

*Primary Examiner*—Cecilia J. Tsang
*Assistant Examiner*—Abdel A. Mohamed
*Attorney, Agent, or Firm*—Quarles & Brady

[57] ABSTRACT

Lyophilized pharmaceutical compositions containing botulinum toxin or botulinum neurotoxin and effective amounts of trehalose and methionine have a shelf life of up to 4 months or more at room temperature and above.

7 Claims, No Drawings

PHARMACEUTICAL COMPOSITIONS OF BOTULINUM TOXIN OR BOTULINUM NEUROTOXIN AND METHODS OF PREPARATION

RELATED CASE

The present application is a continuation-in-part of our co-pending U.S. patent application Ser. No. 08/322,624 filed Oct. 13, 1994, now U.S Pat. No. 5,512,547.

FIELD OF THE INVENTION

The present invention generally relates to botulinum toxin. More particularly, it relates to novel storage stable, lyophilized, pharmaceutical compositions containing either botulinum toxin or botulinum neurotoxin and methods for preparing such compositions.

BACKGROUND OF THE INVENTION

The most serious form of bacterial food poisoning is botulism which is caused by neurotoxins produced by *Clostridium botulinum*. The toxins are usually preformed by the causative organism in foods and subsequently absorbed through the intestinal tract and transported via the circulatory system to motor nerve synapses where their action blocks normal neural transmissions. Various serotypes of *C. botulinum* produce neurotoxins with similar toxic activity but which differ antigenically. Serotype A toxin is the predominant cause of botulism in the United States while type B toxin is the most prevalent in Europe.

Crystalline type A botulinum toxin complex was prepared in 1979 by E. J. Schantz of the Food Research Institute/ Department of Food Microbiology and Toxicology at the University of Wisconsin-Madison. It has been used medically to treat hyperactive muscle disorders such as strabismus, blepharospasm, and spasmodic torticollis. Treatment involves injection of nanogram quantities of the toxin directly into the hyperactive muscles. The toxin inhibits the release of acetylcholine across the synaptic junction causing a decrease in the activity of the injected muscles.

A major drawback to using commercially available botulinum toxin complex preparations for the treatment of hyperactive muscle and other conditions is the development of antibodies or other types of immunity by patients. The proteins of the toxin complex are recognized by patient's immune systems as foreign and they stimulate antibody production. This renders treatment of the various hyperactive muscle disorders with botulinum toxin ineffective. One way to reduce the number of patients developing neutralizing antibodies is to use the purified neurotoxin. Another way would be to have a more shelf-stable product which has a higher specific activity following lyophilization because less of the active protein is denatured. Such a product would not be as antigenic as the currently available product and lesser quantities would be required for treatment.

Botulinal toxin is very susceptible to denaturation due to surface denaturation, heat, and alkaline conditions. Lyophilization or freeze-drying of the toxin complex or the neurotoxin is the most economically sound and practical method of distributing the product in a form that is stable and readily used by the clinician. The current commercial type A botulinal toxin product is made by combining up to 500 ng/ml of type A toxin complex in 5.0 mg/ml human serum albumin (HSA) with 9.0 mg/ml sodium chloride at a pH of 7.3. After dissolution, 0.1 ml is dried to obtain 100±30 active U of toxin, 0.5 mg of HSA, and 0.9 mg of sodium chloride per vial. This product has a saline concentration of 0.9% when reconstituted in 1.0 ml of $dH_2O$. The current commercial formulation which employs the toxin complex has a specific toxicity of about 2.5 U/ng after drying. The considerable loss (up to 90%) of activity during drying causes the formation of inactive toxin that serves as a toxoid inciting antibody formation. The current commercial product must be stored at a temperature of $-10°$ C. or less to maintain the labelled potency for the one year shelf life.

Type A neurotoxin produced by *C. botulinum* is present in the toxin as part of a complex of at least seven different noncovalently bound proteins. The neurotoxin is more active than the toxin complex. High quality type A toxin complex has a specific toxicity of $3\times10^7$ mouse intraperitoneal 50% lethal doses ($LD_{50}$) per mg. The purified neurotoxin, that is the neurotoxin that has been chromatographically separated from the other proteins of the toxin complex, has a specific toxicity of $9\times10^7$ to $1\times10^8$ $LD_{50}$ per mg. In the medical field, a unit (U) is considered to be 1 $LD_{50}$. Toxin titers are determined in female, white mice, 18–22 g in weight according to the method of Schantz and Kautter as described in Association of Official and Analytical Chemistry, vol. 61, p. 96, (1978).

A rabbit model in which repetitive injections of various type A toxin preparations have been given to simulate the treatment of a focal dystonia has been used to assess the immunogenicity of various toxin preparations. The model consists of injecting albino rabbits with sub-lethal doses of the toxin over a period of time and assaying the serum of the animals for the ability to neutralize a small but carefully quantitated amount of purified type A toxin. Our results show that the product presently available in the United States which has the lowest specific toxicity of all preparations tested is the most antigenic of all the preparations tested to date. These results indicate that high specific activity preparations reduce the probability of patients developing neutralizing antibodies. It obviously would be desirable to have higher specific activity preparations than those currently available.

We previously discovered that pharmaceutical compositions made from an aqueous pre-lyophilization formulation containing essentially pure botulinum type A neurotoxin, human serum albumin (HSA), and trehalose provided for the improved recovery of active toxin following lyophilization (>80%). The use of the pure neurotoxin instead of the toxin complex, which is used commercially, reduced the amount of toxin required to obtain the necessary number of active U per vial as mandated by the U.S. Food and Drug Administration. This improvement also reduces the amount of inactive toxin (toxoid) in each vial and thereby lessens the possibility of antibody formation after injection of the preparation into patients.

We also previously discovered that the compositions obtained by adding trehalose to the pre-lyophilization formula had an increased shelf life at higher storage temperatures (e.g., up to 6 months at 37° C.).

BRIEF SUMMARY OF THE INVENTION

We have now discovered that the shelf life of a lyophilized botulinum toxin or neurotoxin containing composition can be improved by the addition of a denaturation preventing amount of a thioalkyl compound, such as methionine or cysteine, to an aqueous pre-lyophilization formulation containing botulinum toxin or neurotoxin, a stabilizing protein, such as albumin, and a polysaccharide sugar, such as trehalose. The addition of methionine has increased the shelf-stability of the compositions at temperatures of 42° C. for up to 3 months or more.

DESCRIPTION OF PREFERRED EMBODIMENT

The preferred pharmaceutical composition of the present invention is a lyophilized solid in a 10 ml glass vial which has the following composition:

Botulinum Type A Neurotoxin, 100 U
Methionine, 1 mg/vial
Trehalose, 10 mg/vial
Serum albumin, 0.5 mg/vial The preferred composition is prepared from a liquid pre-lyophilization formulation containing the same concentrations of the neurotoxin, serum albumin, trehalose and methionine in water.

The Hall A strain of type A *C. botulinum* (deposited with the ATCC) is used to produce the preferred type A neurotoxin. This strain is routinely used for production of type A botulinum toxin due to high toxin titers and the rapid onset of cell lysis (usually within 48 h).

For toxin production, cultures of the Hall A strain are grown statically in 10–20 liter volumes of toxin production medium (TPM) consisting of 2.0% NZ amine or TT (Sheffield Laboratories, Norwich, N.Y.), 1.0% yeast extract (Difco), and 0.5% dextrose, pH 7.37.4, for 5–7 days at 37° C.

To prepare essentially pure type A neurotoxin, the type A toxin complex is first purified according to the method described in the Ph.D. thesis of M. C. Goodnough (Goodnough, M. C. 1994, Characterization and stabilization of *Clostridium botulinum* toxin for medical use. Ph.D. thesis, UW-Madison, as adapted from Tse et al. 1982).

Type A neurotoxin is purified from the associated non-toxic proteins of the complex by a modification of the method of Tse et al. (1982) (Goodnough, M. C., 1994, Thesis, UW, Wis.). Toxin complex is recovered from the DEAE-Sephadex A 50 (Sigma Chemical Co., St. Louis, Mo.), pH 5.5, column and is precipitated by addition of 39 g of solid ammonium sulfate/100 ml. The precipitated toxin complex is collected by centrifugation, dialyzed against 25 mM sodium phosphate, pH 7.9, and applied to a DEAE-Sephadex A50 column equilibrated with the same buffer. Toxin is separated from the non-toxic proteins of the complex and eluted from the column with a linear 0–0.5M sodium chloride gradient. Partially purified neurotoxin is recovered from the DEAE-Sephadex A50 column at pH 7.9 and dialyzed against 25 mM sodium phosphate, pH 7.0. The dialyzed toxin is applied to SP-Sephadex C50 (Sigma Chemical Co.) in 25 mM sodium phosphate, pH 7.0. Contaminating material does not bind to the column under these conditions. The neurotoxin is eluted with a linear 0–0.25M sodium chloride gradient. The neurotoxin can be further purified by metal affinity chromatography, gel filtration or other methods of protein chromatography.

For lyophilization, the pre-lyophilization formulation is placed in glass vials with Teflon lined screw cap closures fastened loosely, and the samples are quickly frozen in liquid nitrogen. The frozen samples are placed into a lyophilization flask which is then immersed in liquid nitrogen. When the pressure drops below ca. 60 mTorr, the liquid nitrogen jacket is removed. Pressure is maintained at or below 30–60 mTorr and- condenser temperature constant at –60° C. The vials and their contents are allowed to come to room temperature and drying continued at ambient temperature over the next 18–24 h. At that time the flask is removed and the vials tightly capped.

Vials of lyophilized product made from the described pre-lyophilization formulation containing methionine and identical formulations not containing methionine were stored at various temperatures to investigate the effect of the methionine on the shelf-stability of the lyophilized product. In these cases, the tightly capped vials were placed into plastic bags, sealed and stored at various temperatures (–20°, 4°, 37° or 42° C.) and the contents assayed for toxicity at various time points. The lyophilized preparations were then reconstituted in 1.0 ml of distilled water. The use of 0.85% saline for reconstitution gave equivalent results. The resulting solutions were transparent and contained no particulates. These solutions were titrated by the same method used for the pre-lyophilization formulation.

The percent recovery of activity (calculated as number of mouse intraperitoneal lethal doses per vial after lyophilization divided by the number of mouse intraperitoneal lethal doses before lyophilization ×100) following lyophilization of different type A and B neurotoxin formulations are shown in Table 1.

TABLE 1

| Excipient/ Starting toxin neurotoxin type[a] | concentration[b] | pH | % recovery[c] |
|---|---|---|---|
| 1. bovine serum albumin/ type A | 200 | 6.4 | 90 |
| 2. bovine serum albumin/ type B | 100 | 6.4 | 80 |
| 3. human serum albumin/ type A | 1,000 | 6.4 | 90 |
| 4. human serum albumin/ type B | 100 | 6.4 | 90 |
| 5. bovine serum albumin, trehalose/ type A | 500 | 5.7 | >90 |
| 6. bovine serum albumin, maltotriose type A | 250 | 7.0 | 90 |
| 7. bovine serum albumin, methionine/ type A | 250 | 6.8 | 90 |
| 8. bovine serum albumin, trehalose, methionine/ type A | 250 | 6.8 | 90 |

[a] bovine and human serum albumin concentration was 9.0 mg/ml, carbohydrate concentration was 100 mg/ml in all cases and methionine concentration was 10 mg/ml;
[b] mouse intraperitoneal lethal doses/vial;
[c] (number of mouse lethal doses/vial after lyophilization + number of mouse lethal doses before lyophilization) × 100 immediately following lyophilization.

The primary advantages of the preferred compositions of the present invention are their high percentage recovery of biologically active neurotoxin and their long-term stability (shelf life) for up to and exceeding three months at temperatures as high as 37° C. to 42° C. In contrast, the current commercial product must be stored at temperatures of –10° C. or less.

The exact mechanism by which the methionine further improves the shelf life of the compositions containing trehalose is not known. However, the improvement does appear to be linked to the presence of the thioalkyl group in the amino acid. The recovery of activity following storage of lyophilized type A neurotoxin products at different temperatures is shown in TABLE 2.

TABLE 2

| Excipient combination from Table 1 | Storage Temperature | Days of storage | % recovery* |
|---|---|---|---|
| 1. BSA alone | −20° C. | 10 | 90 |
|  |  | 60 | 90 |
|  |  | 125 | 90 |
|  | 4° C. | 60 | 90 |
|  |  | 100 | 50 |
|  |  | 125 | 25 |
|  | 37° C. | 15 | 75 |
|  |  | 60 | 50 |
|  |  | 125 | 25 |
| 5. BSA + trehalose | 4° C. | 60 | 75 |
|  |  | 100 | 75 |
|  |  | 125 | 75 |
|  | 37° C. | 60 | 90 |
|  |  | 100 | 90 |
|  |  | 125 | 90 |
| 7. BSA + methionine | 25° C. | 15 | 75 |
|  |  | 30 | 50 |
|  |  | 60 | 50 |
|  | 37° C. | 15 | 75 |
|  |  | 30 | 50 |
|  |  | 60 | 25 |
|  | 42° C. | 15 | 50 |
|  |  | 30 | 25 |
| 8. BSA + trehalose + methionine | 25° C. | 15 | 90 |
|  |  | 30 | 90 |
|  |  | 60 | 90 |
|  | 37° C. | 15 | 90 |
|  |  | 30 | 90 |
|  |  | 60 | 90 |
|  | 42° C. | 15 | 90 |
|  |  | 30 | 90 |
|  |  | 60 | 90 |

*(number of mouse lethal doses/vial after lyophilization and storage under given conditions listed ÷ number of mouse lethal doses before lyophilization) × 100

In addition to type A, there are six other serotypes of the botulinum toxin with similar toxic activity but which differ antigenically. They are type A, B, C, D, E, F and G. Type A is the predominant toxin in cases of botulism in the United States, and type B toxin is most prevalent in Europe. The symptoms for the disease caused by the various serotypes are about the same. Therefore, in some instances it may be desirable to use one of the other serotypes in the pharmaceutical compositions of the present invention.

The preferred polyglucose sugar is trehalose. However, in some cases other sugars such as maltotriose can be used. The amount of trehalose to be used is preferably from about 10 mg to about 150 mg per ml of the pre-lyophilized liquid formulation. Especially preferred is the use of about 100 mg/ml.

The preferred thioalkyl compound is methionine; however, in some cases it may be desirable to use cysteine. The amount of methionine which is effective to prevent denaturation of the compound having botulinum toxicity is preferably from about 1 mg to about 10 mg per ml of the pre-lyophilized formulation. Especially preferred is the use of about 10 mg of methionine per ml.

The antigenicity of various toxin preparations (containing low or high specific toxicities) was evaluated in rabbits by repetitive injection of sublethal doses of toxin simulating treatment of a focal dystonia with botulinal toxin. The samples were standardized to contain the same number of active lethal doses in order that the immune response from the rabbits could be compared.

Total toxin concentration for each preparation (i.e. both active and inactive) was determined using an enzyme-linked immunosorbent assay (ELISA) specific for type A botulinal toxin.

Other test results show that the immune response of rabbits to botulinal toxin is dependent on concentration of the toxin (active+inactive) injected as well as the number of times the animal is exposed to that concentration. From these results it follows that the higher the specific activity of the lyophilized/reconstituted toxin product, the less antigenic material the patient is exposed to for a given dosage and the smaller the chances of patients developing neutralizing antibodies. Thus, it is preferred to have lyophilized pharmaceutical compositions of essentially pure neurotoxin which permit the recovery of a high percentage of the starting activity and which contain trehalose and methionine so that they can be stored at room temperature or higher for up to 3 months or more.

It will be apparent to those skilled in the art that a number of modifications and changes can be made without departing from the spirit and scope of the present invention. Therefore, it is intended that the invention be limited only by the claims.

We claim:

1. A lyophilized solid pharmaceutical composition comprising:

(a) a compound having botulinum toxicity;

(b) a stabilizing protein;

(c) a polysacchride sugar; and (d) a thioalkyl compound;

said thicalkyl compound being present in an amount effective to prevent the denaturation of the compound at storage temperatures between 25° C. and 42° C.

2. A composition of claim 1 in which the stabilizing protein is human serum albumin.

3. A composition of claim 1 in which the thioalkyl compound is selected from the group consisting of methionine and cysteine.

4. A composition of claim 1 in which the polysaccharide sugar is trehalose.

5. A composition of claim 1 in which the compound having botulinum toxicity is type A botulinum neurotoxin.

6. A composition of claim 1 in which the compound having botulinum toxicity is type A botulinum toxin complex.

7. A lyophilized solid pharmaceutical composition of botulinum neurotoxin which is stable at room temperature for up to four months without losing potency, said composition comprising pure type A botulinum neurotoxin and effective amounts of trehalose and methionine to increase the storage stability of the composition at room temperature.

* * * * *

UNITED STATES PATENT AND TRADEMARK OFFICE
CERTIFICATE OF CORRECTION

PATENT NO. : 5,756,468
DATED : May 26, 1998
INVENTOR(S) : Eric A. Johnson and Michael C. Goodnough It is certified that error appears in the above-indentified patent and that said Letters Patent is hereby corrected as shown below:

Column 2, Line 66:
"polysaccheride" should be --polysaccharide--.

Column 3, Line 63:
"and-" should be --and--.

Column 6, Line 36:
"thicalkyl" should be --thioalkyl--.

Signed and Sealed this

Eighteenth Day of August, 1998

Attest:

BRUCE LEHMAN

Attesting Officer    Commissioner of Patents and Trademarks